United States Patent

Bröcker et al.

[11] Patent Number: 6,150,564
[45] Date of Patent: Nov. 21, 2000

[54] SELECTIVE LIQUID-PHASE HYDROGENATION OF α,β-UNSATURATED CARBONYL COMPOUNDS

[75] Inventors: Franz Josef Bröcker, Ludwigshafen; Gerd Kaibel, Lampertheim; Werner Aquila, Mannheim; Hartwig Fuchs, Ludwigshafen; Günter Wegner, Römerberg; Manfred Stroezel, Ilvesheim, all of Germany

[73] Assignee: BASF Aktiengesellschaft, Ludwigshafen, Germany

[21] Appl. No.: 09/275,867

[22] Filed: Mar. 25, 1999

[30] Foreign Application Priority Data

Apr. 2, 1998 [DE] Germany ............ 198 14 879

[51] Int. Cl.⁷ .................................................. C07C 45/62
[52] U.S. Cl. ........................................... 568/462; 568/396
[58] Field of Search .................................. 568/458, 459, 568/462, 395, 396

[56] References Cited

U.S. PATENT DOCUMENTS

| | | | |
|---|---|---|---|
| 4,320,228 | 3/1982 | Horner et al. | 568/459 |
| 4,847,016 | 7/1989 | Göbel | 200/409 |

FOREIGN PATENT DOCUMENTS

| | | |
|---|---|---|
| 2201014 | 9/1997 | Canada . |
| 0 024 651 | 3/1981 | European Pat. Off. . |
| 0 798 039 | 10/1997 | European Pat. Off. . |
| 2 247 445 | 5/1975 | France . |
| 2 114 211 | 10/1971 | Germany . |
| 28 39 474 | 3/1980 | Germany . |
| 29 36 362 | 4/1981 | Germany . |
| 226 872 | 9/1985 | Germany . |
| 195 30 329 | 2/1997 | Germany . |
| 196 41 707 | 4/1998 | Germany . |

*Primary Examiner*—Sreeni Padmanabhan
*Attorney, Agent, or Firm*—Oblon, Spivak, McClelland, Maier & Neustadt, P.C.

[57] ABSTRACT

The invention relates to a process for the selective liquid-phase hydrogenation of α,β-unsaturated carbonyl compounds of the formula I,

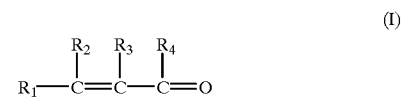
(I)

where $R_1$ is hydrogen or an organic radical, and $R_2$, $R_3$ and $R_4$, independently of one another, are hydrogen or a $C_1$— to $C_4$—alkyl group, to saturated carbonyl compounds of the formula II

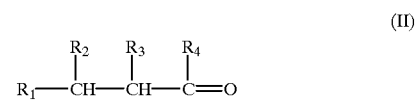
(II)

using hydrogen in the presence of a pulverulent palladium and/or rhodium catalyst and in the presence of an organic base. The process is carried out in a packed bubble column reactor (1, 2) with product recycling (11, 17) and circulating hydrogen gas (4, 15, 16). It is particularly suitable for the selective hydrogenation of citral to citronellal.

29 Claims, 2 Drawing Sheets

SELECTIVE LIQUID-PHASE HYDROGENATION OF α,β-UNSATURATED CARBONYL COMPOUNDS

The present invention relates to a process for the selective liquid-phase hydrogenation of α,β-unsaturated carbonyl compounds of the formula I

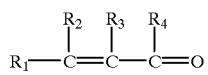
(I)

to the corresponding saturated carbonyl compounds of the formula II

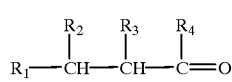
(II)

using hydrogen in the presence of a pulverulent palladium and/or a rhodium catalyst and in the presence of an organic base. The invention specifically relates to the selective hydrogenation of citral to citronellal.

Processes for the selective hydrogenation of α,β-unsaturated carbonyl compounds using hydrogen in the liquid phase are described, for example, in DE-A-21 14 211 and DE-A-28 39 474. Both processes operate batchwise in the presence of a palladium catalyst and a base, the process of DE-A-28 39 474 using from 15 to 50% by weight of a tertiary amine, based on the starting material, exhibiting improved selectivity and space-time yield of the hydrogenation reaction.

However, even this improvement does not give satisfactory reaction times. Although the reaction times can be shortened by using larger amounts of the palladium catalyst, this is, however, uneconomical owing to the high catalyst costs, and in addition larger amounts of catalyst are disadvantageous in view of the problems of handling solids. Neither is successful regeneration of the deactivated catalyst generally possible.

It is therefore an object of the present invention to hydrogenate α,β-unsaturated carbonyl compounds of the formula (I) to the corresponding α,β-unsaturated carbonyl compounds of the formula (II) in a more economical manner, while improving the space-time yield and reducing the investment costs.

Specifically, it is an object of the present invention to provide a more economical process for the hydrogenation of citral to citronellal.

We have found that this object is achieved by a process for the selective liquid-phase hydrogenation of α,β-unsaturated carbonyl compounds of the formula (I)

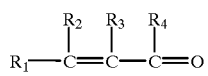
(I)

where $R_1$ is hydrogen or an organic radical, and $R_2$, $R_3$ and $R_4$, independently of one another, are hydrogen or a $C_1$— to $C_4$—alkyl group, to saturated carbonyl compounds of the formula (II)

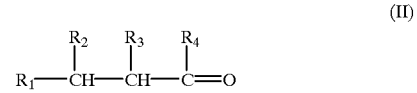
(II)

using hydrogen in the presence of a pulverulent palladium and/or rhodium catalyst and in the presence of an organic base, which comprises carrying out the hydrogenation in a packed bubble column reactor with product recycling and circulating hydrogen gas.

It has been found that the rate-determining step in the process as a whole, namely diffusion of the gaseous hydrogen to the catalyst surface, can be accelerated by carrying out the process in a packed bubble column reactor with product recycling and circulating hydrogen gas. As the reaction proceeds, the hydrogen concentration in the liquid in the vicinity of the catalyst surface drops. This low-hydrogen film at the catalyst surface can then, through the novel use of a packed bubble column reactor with product recycling and circulating hydrogen gas, be swirled around in such a way that exchange with hydrogen-saturated liquid from the outside becomes possible. A crucial role is played here by the increased relative motion of the catalyst particles with respect to the liquid phase and the hydrogen gas bubbles, which is caused by the catalyst particles being slowed down and briefly held at the packing channel walls. The improved hydrodynamics mean that the catalyst is utilized particularly well.

The novel process may in principle be used for all α,β-unsaturated carbonyl compounds of the formula (I), the shortened reaction time improving the selectivity with respect to hydrogenation of the double bond, i.e. the individual reaction with the larger rate constant. In a preferred embodiment, the starting material citral is converted to citronellal.

The pulverulent palladium and/or rhodium catalyst can be used in the form of a supported or unsupported catalyst, preferred support materials being carbon, zirconium dioxide or titanium dioxide. It is particularly advantageous to use catalyst supports having a mean particle size of from 0.1 to 300 μm, preferably from 0.5 to 100 μm. These catalyst particles, with their high surface area per unit volume, result in good space-time yields since they are able, when flowing through the openings and channels in the bubble column reactor packing, to execute relative movements with respect to the liquid phase and the hydrogen gas bubbles.

The hydrogenation is carried out in a packed bubble column reactor. Particularly suitable packing has openings or channels whose hydraulic diameter is from 0.5 to 20 mm, preferably from 1 to 10 mm, particularly preferably from 1 to 3 mm. The hydraulic diameter is defined as the quotient of the quadruple opening cross section and its circumference. The suspended catalyst particles are slowed down in the packing openings or channels by collisions with the channel walls and by brief holding. It has been observed that, for hydraulic diameters in the above range, on average a proportion of about 15 to 16% by weight of the catalyst is held on the packing walls at any one time.

This effect can be further improved by increasing the surface roughness of the walls. Preferred wall materials have surface roughness values in the range from 0.1 to 10 times, preferably from 0.5 to 5 times, the mean particle size of the suspended catalyst particles. Particularly suitable wall materials are metallic and have a surface with a mean roughness $R_a$, measured in accordance with DIN EN ISO 4287, of from 0.001 to 0.01 mm.

Suitable packing materials are metallic materials, plastics, ceramics and/or inorganic fibers, in particular carbon or asbestos substitutes.

The packing can be in the form of foils, gauzes or meshes, as are already known in principle, i.e. with respect to their geometrical shape, from distillation or extraction technology. Packing elements of this type, which offer the advantage of low pressure loss, are, for example, wire mesh packing of the Montz A3 and Sulzer BX, DX and EX type. For the purposes of the present invention, however, the packing basically has a hydraulic diameter which is essentially smaller, generally by a factor of from 2 to 10, than comparable internals in the area of distillation or extraction technology. Wire mesh packing is particularly advantageous. For the purposes of the present invention, however, mesh packing can also be replaced by packing made from other woven, knitted or felted, liquid-permeable materials. In other suitable packing, flat metal sheets, preferably without perforations or other relatively large openings, are used, for example as in the Montz B1 or Sulzer Mellapak types. Also advantageous is packing made from expanded metal, for example packing of the Montz BSH type. Here too, openings, for example perforations, must be kept appropriately small. The crucial factor for the suitability of packing for the purposes of the present invention is not its geometry, but the opening sizes or channel widths formed in the packing for flow passage.

In a preferred process, the liquid phase is pumped through the packed bubble column reactor at a superficial velocity of from 100 to 500 $m^3/m^2.h$, preferably from 150 to 300 $m^3/m^2.h$.

The circulating hydrogen gas is fed to the liquid phase containing suspended pulverulent catalyst at a preferred superficial velocity of 0.5 to 15 cm/s, preferably from 2.5 to 10 cm/s. The circulating hydrogen gas is preferably introduced via a gas jet compressor, which effects intensive mixing with the liquid phase and the catalyst suspended therein.

The hydrogenation is preferably carried out at a hydrogen partial pressure of from 1 to 200 bar, preferably from 1 to 100 bar, particularly preferably from 1 to 10 bar.

Preferred reaction temperatures are from 25 to 150° C., particularly from 50 to 100° C.

The process can be carried out either batchwise or continuously. The continuous procedure is particularly advantageous. In this, the spent catalyst can be separated off by the particularly favorable method of cross-flow filtration.

The liquid phase containing suspended catalyst and the hydrogen are preferably circulated in cocurrent. It is particularly advantageous to feed the starting materials to a vertical bubble column reactor from below.

BRIEF DESCRIPTION OF THE DRAWINGS

The invention is illustrated in greater detail below with reference to an illustrative embodiment and a figure, in which, in detail:

FIG. 1 shows, by way of example, a diagrammatic representation of a plant having a bubble column reactor 1 operated batchwise, which is filled with packing 2 whose geometry is comparable to that of the Montz-Pak type A3-1200 distillation packing.

Figure 1:
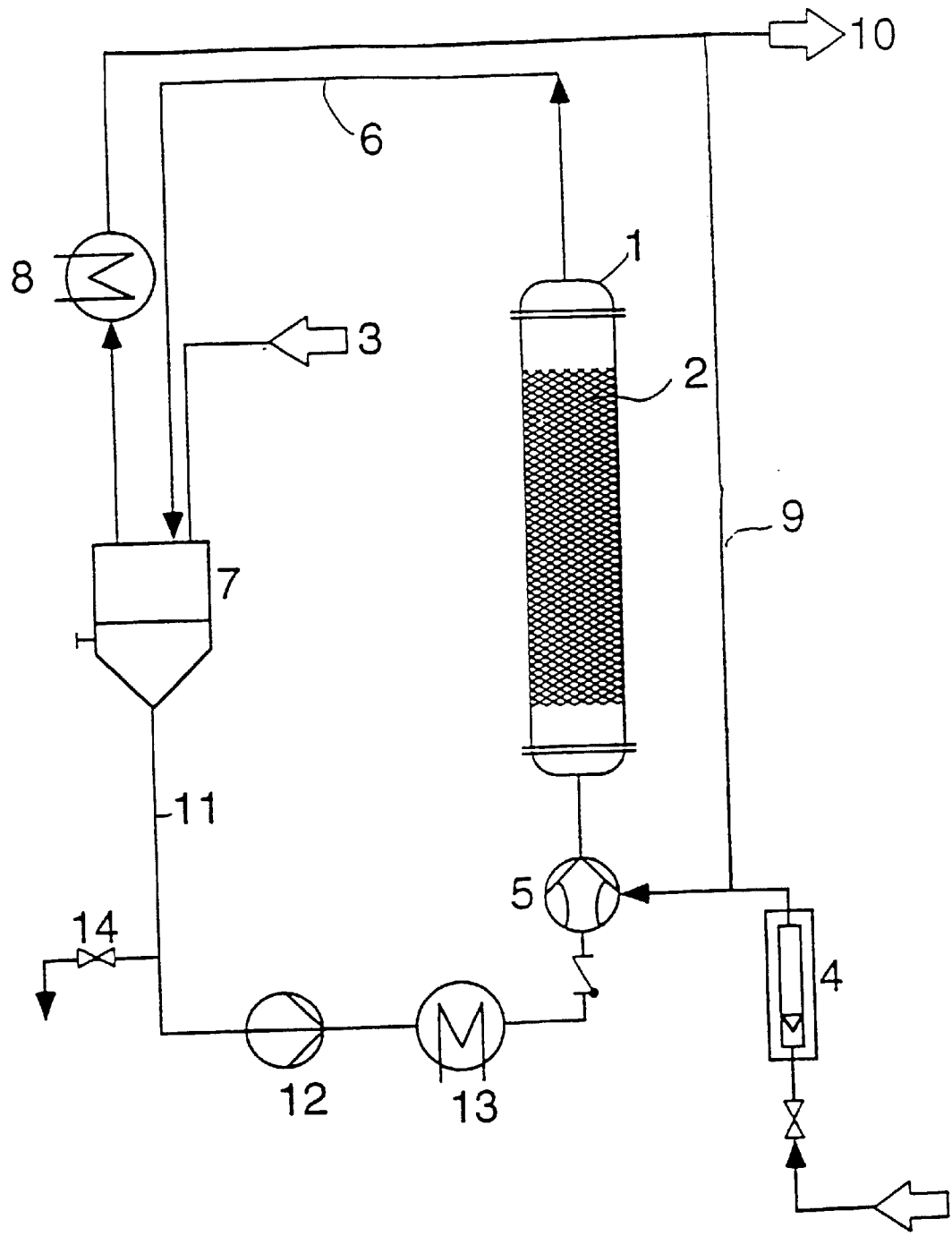
FIG. 1 shows a diagrammatic representation of a plant for a batch process in accordance with the invention.

In order to carry out the hydrogenation, the storage tank 7 is first filled with starting material, amine and suspension catalyst via the fill line 3. By means of the circulation pump 12, the reaction mixture is pumped via the preheater 13 and the gas jet compressor 5 into the reactor and from the latter back via the circulation line 6 into the storage tank 7. Here, the unreacted hydrogen is separated off and fed back via the circulating gas line 9 to the mixing nozzle 5 and thus to the reactor inlet and mixed intimately with the circulating suspension. The hydrogen consumed is replaced continuously via the fresh hydrogen line 4. A certain amount of offgas can be passed through the offgas line 10 in order to prevent accumulation of inert gases.

When the hydrogenation is complete, the suspension is discharged via the withdrawal line 14.

The high space-time yield in this procedure is achieved by circulating the suspension at a rate of from 100 to 500 $m^3/m^2.h$ and preferably from 150 to 300 $m^3/m^2.h$, based on the free reactor cross section, and distributing the hydrogen optimally in the suspension via the gas jet compressor 5.

This procedure generates increased turbulence in the gas-containing suspension within the packing. The catalyst particles execute an increased relative motion with respect to the liquid because, in the narrow openings and channels of the packing, they experience a deceleration with respect to the liquid surrounding them and the rising gas bubbles.

Figure 2:
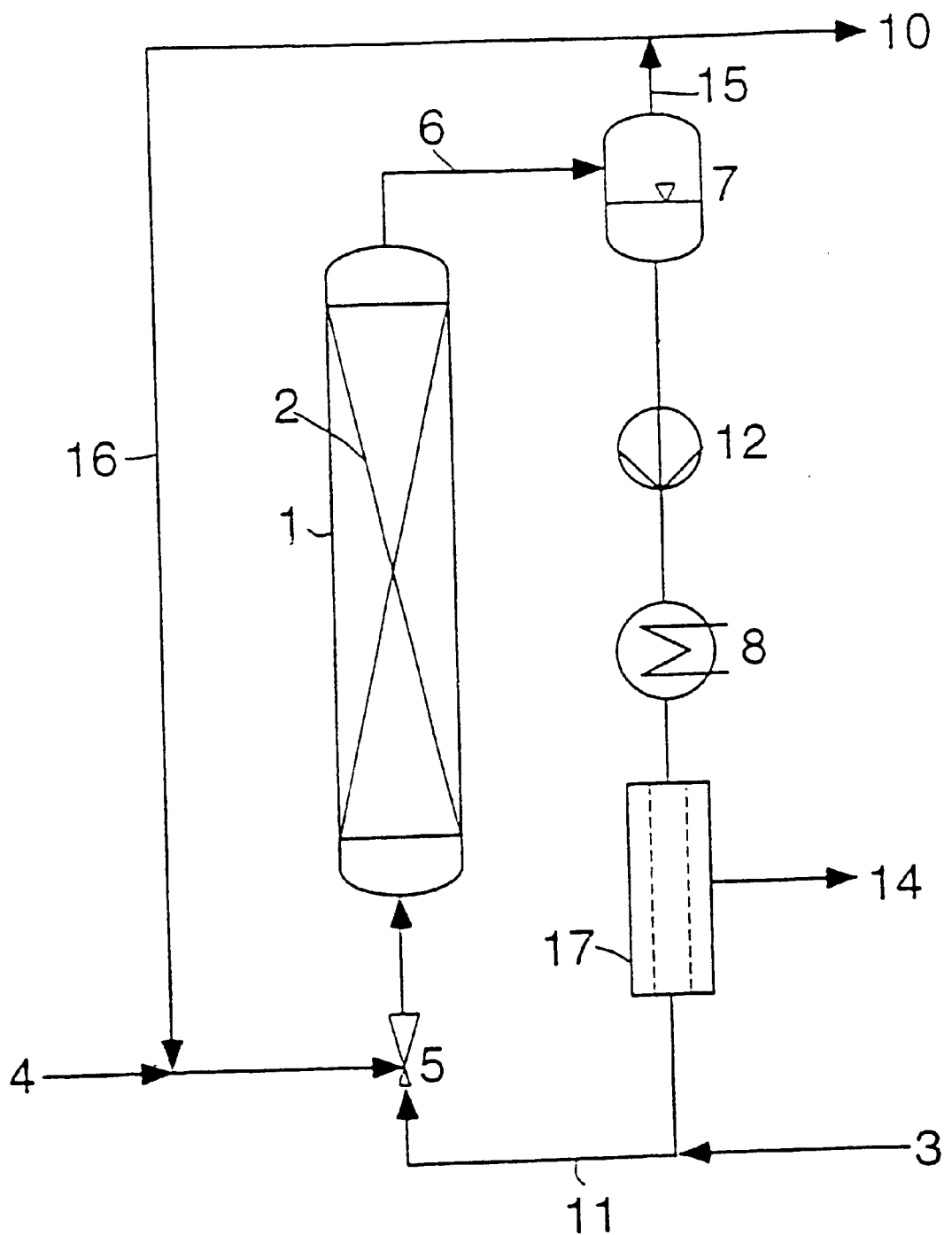
FIG. 2 shows a diagrammatic representation of a plant for the particularly preferred continuous implementation of the process of the invention.

FIG. 2 shows a particularly advantageous continuous procedure. The reactor 1 is filled with packing 2 and provided with a liquid and gas circulation. Firstly, the entire circuit is filled with suspension, advantageously prehydrogenated product and suspension catalyst, via the feed line 3. By means of the circulation pump 12, the suspension is fed via the preheater 8 and the cross-flow filtration unit 17 to the mixing nozzle 5. The mixing nozzle is a gas jet compressor which sucks the hydrogen in via the circulating gas lines 15 and 16 and mixes it vigorously with the suspension. If the circulation is implemented in this way, the starting material to be hydrogenated is introduced via the feed line 3. The requisite hydrogen is fed in continuously via the $H_2$ line 4 by means of a pressure maintenance system.

Suspension and hydrogenation water are mixed intimately in reactor 1 in the openings and channels of the packing, resulting in correspondingly good hydrogenation. The reactor products enter the separator 7 via line 6. In the separator, the gas phase is separated off and fed back to the reactor inlet via the circulating gas lines 15 and 16. A certain amount of offgas can be removed via the offgas line 10. This prevents accumulation of inert gases in the hydrogen.

The suspended catalyst remains in the reactor system by being retained by the cross-flow filter 17. The catalyst-free product is discharged as permeate via 14.

For a production plant with packed bubble column reactor as shown in FIG. 2, the investment costs are only about ¼ of the costs for a conventional stirred reactor plant of the same space-time yield.

Example 1

The reactor of an apparatus which, in accordance with FIG. 1, is suitable for batch hydrogenation, was charged with five monoliths having a diameter of 27 mm and a height of 5 cm and consisting of $V_2A$ mesh, material No. 4301, having a cross-channel structure (module 1.0 mm). The plain-woven wire mesh has a mesh width of 0.18 mm and a wire diameter of 0.105 mm. The apparatus was charged via a fill hopper with 550 ml of citral solution consisting of 70% by weight of citral, 27% by weight of methanol and 3% by weight of trimethylamine, and 5 g of pulverulent palladium/carbon catalyst (5% by weight of Pd). The latter had a particle size distribution of between 0.001 and 0.2 mm with a 50% value of 0.012 mm, measured using a Cilas laser spectrometer by the sedimentation method in accordance with DIN standard 66111. After injection of hydrogen to 8 bar via the $H_2$ feed line 4, the circulation pump 12 was switched on and a flow rate of 200 $m^3/m^2.h$, based on the free reactor cross section, was established. The nozzle of the gas jet compressor then sucked hydrogen in via the circulating gas line 9 and aerated the reactor at a gas velocity of 5.5 cm/s. By means of the preheater 13, the reactor inlet temperature was raised to 70° C. During the hydrogenation, samples were taken from the circulation at certain time intervals via the valve 14 and analyzed by gas chromatography.

After 2.75 h, a citral conversion of 99.5% and selectivity of 94% had been achieved. The space-time yield, based on the Pd/C catalyst, was 22.4 kg of citral/$kg_{cat}$·h.

Comparative example 1

6.9 l of citral solution consisting of 70% by weight of citral, 27% by weight of methanol and 3% by weight of trimethylamine, and 55 g of pulverulent palladium/ carbon catalyst (5% by weight of Pd) were introduced into a 10 l stirred reactor with gas dispersion stirrer. The particle size of the catalyst corresponded to that in Example 1.

After hydrogen had been injected and the reactor had been heated to 70° C., the mixture was hydrogenated at 8 bar of $H_2$ with stirring at 800 revolutions per minute. The progress of the hydrogenation was analyzed by means of samples taken at certain time intervals and analyzed by gas chromatography. After 19 hours, the citral conversion was 99.7% and the product selectivity was 92.9%. The space-time yield, based on the pulverulent Pd/C catalyst, was 3.68 $kg_{citral}/kg_{cat}*h$.

We claim:

1. A process for the selective liquid-phase hydrogenation of α,β-unsaturated carbonyl compounds of the formula (I)

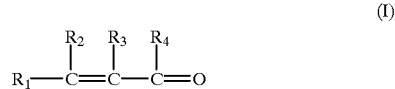

(I)

wherein $R_1$ is hydrogen or an olefinically unsaturated hydrocarbyl group, and $R_2$, $R_3$ and $R_4$, independently of one another, are hydrogen or a $C_1$–$C_4$—alkyl group, to saturated carbonyl compounds of the formula (II)

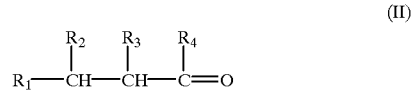

(II)

comprising:

hydrogenating said α,β-unsaturated carbonyl compound in the presence of a pulverulent palladium and/or rhodium catalyst and in the presence of an organic base under liquid phase conditions in a packed bubble column reactor with hydrogen fed into the reactor at a superficial velocity of 0.5 to 15 cm/s and circulating of the liquid phase containing product at a superficial velocity of 100 to 500 $m^3/m^2$·h with recycling of the product and circulating hydrogen gas within the reactor.

2. The process as claimed in claim 1, wherein the packing in the bubble column reactor has openings and channels whose hydraulic diameter is from 0.5 to 20 mm.

3. The process as claimed in claim 1, wherein the walls of the openings or channels of the packing in the bubble column reactor have surface roughness values in the range from 0.1 to 10 times the mean particle size of the pulverulent catalyst particles.

4. The process as claimed in claim 1, wherein the walls of the openings or channels of the packing in the bubble column reactor are metallic and have a mean roughness $R_a$, measured in accordance with DINEN ISO 4287, of from 0.001 to 0.01 mm.

5. The process as claimed in claim 1, wherein the packing in the bubble column reactor is made of metallic materials, plastics, ceramics and/or inorganic fibers.

6. The process as claimed in claim 5, wherein the packing is a foil, gauze or mesh.

7. The process as claimed in claim 1, wherein the palladium and/or rhodium catalyst is supported, the support material used being, carbon, zirconium dioxide or titanium dioxide, having a mean particle size of from 0.1 to 300 μm.

8. The process as claimed in claim 7, wherein the supported catalyst contains from 0.01 to 10% by weight of palladium and/or rhodium.

9. The process as claimed in claim 1, wherein the liquid phase is circulated at a superficial velocity of from 100 to 500 $m^3/m^2$·h.

10. The process as claimed in claim 1, wherein the hydrogen is fed in at a superficial velocity of from 0.5 to 15 cm/s by means of a gas jet compressor.

11. The process as claimed in claim 1, wherein the hydrogenation is carried out at a hydrogen partial pressure of from 1 to 200 bar.

12. The process as claimed in claim 1, wherein the hydrogenation is carried out at a temperature of from 25 to 150° C.

13. The process as claimed in claim 1, which is carried out continuously.

14. The process as claimed in claim 1, wherein the liquid phase and the hydrogen are conveyed in cocurrent, from bottom to top through a vertical bubble column reactor.

15. The process as claimed in claim 1, wherein the α,β-unsaturated carbonyl compound of the formula (I) is citral.

16. The process as claimed in claim 2, wherein said diameter ranges from 1 to 10 mm.

17. The process as claimed in claim 16, wherein said diameter ranges from 1 to 3 mm.

18. The process as claimed in claim 3, wherein said surface roughness ranges from 0.5 to 5 times the mean particle size of the pulverulent catalyst particles.

19. The process as claimed in claim 7, wherein said mean particle size ranges from 0.5 to 100 μm.

20. The process as claimed in claim 7, wherein said amount of palladium and/or rhodium ranges from 0.2 to 5% by weight.

21. The process as claimed in claim 20, wherein said amount of palladium and/or rhodium ranges from 0.5 to 1% by weight.

22. The process as claimed in claim 9, wherein said superficial velocity ranges from 150 to 300 $m^3/m^2$·h.

23. The process as claimed in claim 10, wherein said superficial velocity ranges from 2.5 to 10 cm/s.

24. The process as claimed in claim 11, wherein said partial pressure ranges from 1 to 100 bar.

25. The process as claimed in claim 24, wherein said partial pressure ranges from 1 to 10 bar.

26. The process as claimed in claim 12, wherein said temperature ranges from 50 to 100° C.

27. The process as claimed in claim 1, wherein the liquid phase is circulated at a superficial velocity of 150 to 300 $m^3/m^2$·h.

28. The process as claimed in claim 1, wherein hydrogen is fed into the reactor at a superficial velocity of 2.5 to 10 cm/s.

29. The process as claimed in claim 5, wherein the packing in the bubble column reactor is made of carbon or asbestos substitutes.

* * * * *